United States Patent [19]
Farese et al.

[11] Patent Number: 5,913,821
[45] Date of Patent: Jun. 22, 1999

[54] DIAGNOSTIC METHOD AND APPARATUS FOR ASSESSING CANINE HIP DYSPLASIA

[75] Inventors: James P. Farese; Rory J. Todhunter; George Lust, all of Ithaca, N.Y.

[73] Assignee: Cornell Research Foundation, Inc., Ithaca, N.Y.

[21] Appl. No.: 08/949,939

[22] Filed: Oct. 14, 1997

[51] Int. Cl.[6] .................................................. A61B 5/00
[52] U.S. Cl. ........................................... 600/425; 600/595
[58] Field of Search ................................... 600/407, 425, 600/587, 592, 595; 128/898

[56] References Cited

U.S. PATENT DOCUMENTS 5,482,055   1/1996   Smith ....................................... 600/595

OTHER PUBLICATIONS

Smith et al, Am. J. Vet. Res. vol. 54 pp. 1021–1042, 1993.
Smith et al, Am. Vet. Med. Assoc. vol. 196 pp. 59–70, 1990.
Lust et al, Am. J. Vet. Res. vol. 54 pp. 1990–1999, 1993.
Chalman et al, J. Am. Anim. Health Assoc. vol. 21 pp. 671–676, 1985.
Barlow et al J. Bone Joint Surg. vol. 44 pp. 292–301, 1962.
Corley et al Hip Dysplasia: a guide for dog breeders and owners, 2nd edition pp. 8–11, 1989.

*Primary Examiner*—Ruth S. Smith
*Attorney, Agent, or Firm*—Hodgson, Russ, Andrews, Woods & Goodyear, LLP

[57] ABSTRACT

A method for measuring functional laxity in a dog for determining presence of or absence of canine hip dysplasia is provided by placing the dog in a weight-bearing position; and assessing hip joint subluxation by an imaging technique by estimating a degree of dorsolateral subluxation for each hip joint of the positioned dog, with the degree of dorsolateral subluxation determined by measuring the portion of femoral head medial to the acetabulum. Also provided is an apparatus for placement and positioning of a dog, being evaluated for canine hip dysplasia, in a weight-bearing position.

10 Claims, 8 Drawing Sheets ically develops during the first 6 to 12 months of age, whereas symptoms may develop years later. There are several reasons why early diagnosis (e.g., less than one year of age) of canine hip dysplasia is desirable and useful. For example, a diagnostic procedure that can accurately and sensitively identify affected dogs at an early age could enable dog breeders to reduce the prevalence of the disease by choosing not to breed affected dogs. Additionally, there are some treatment options available for dogs affected by canine hip dysplasia. One such treatment is a surgical procedure, known as BOP (Biocompatible Osteoconductive Polymer) Shelf Arthroplasty, in which a polymer is used to rebuild the defective hips of dysplastic dogs so that subluxation is then prevented. Another treatment relates to management of the physical activity and weight (by diet and choice of exercise) of the affected dog in attempts to limit strain on the affected hip joints.

DIAGNOSTIC METHOD AND APPARATUS FOR ASSESSING CANINE HIP DYSPLASIA

FIELD OF THE INVENTION

This invention relates to a novel imaging technique for veterinary use. More particularly, the present invention relates to the use of an imaging technique such as radiography and/or computed tomography (CT) to evaluate hip laxity and conformation in a diagnostic procedure for canine hip dysplasia.

BACKGROUND OF THE INVENTION

Canine hip dysplasia is a common orthopedic disease affecting millions of dogs in the United States alone. Canine hip dysplasia affects many breeds of dogs, but is of particular high incidence in dogs large in size. Included in the more than 80 canine breeds affected are German shepherd, Newfoundland, Old English sheepdog, English bulldog, Labrador retriever, other retriever breeds, Irish setter, Great Dane, and St. Bernard. The disease is characterized by laxity and incongruity of the hip joint resulting in degeneration of joint tissues. Osteoarthritis develops as a result of the abnormal positioning of the head of the femur in relation to the joint due to laxity, and resulting in the erosion of joint cartilage, and inflammation of the synovium. The development in a dog of osteoarthritis in a dysplastic hip joint is a benchmark sign of canine hip dysplasia.

Canine hip dysplasia is believed to be hereditary disease of complex genetic and environmental bases. Clinical symptoms range from mild hip joint discomfort to severe and debilitating; and the disease is the most common cause of rear-end lameness. However, in most cases the clinical symptoms appear in affected dogs much later in life than initiation of the disease. In that regard, canine hip dysplasia typ A current method for detecting hip dysplasia, disclosed in U.S. Pat. No. 5,482,055, is based on compression-distraction stress radiography. This method measures joint laxity that is related to the presence of absence of osteoarthritis (Smith et al., 1993, *Am. J. Vet. Res.* 54:1021–42; Smith et al., 1990, *J. Am. Vet. Med. Assoc.* 196:59–70). This stress method elicits passive laxity, which is the maximal lateral displacement of the femoral heads that occurs when a force is used to distract the hip joint. An adjustable device, a "distractor", is used to reveal passive laxity, and to quantitate lateral displacement of the femoral head by a measurement called the "distraction index". This index is used as a measure of passive laxity and as a predictive value, wherein below a certain value it is unlikely that the dog will develop osteoarthritis. For example, in Labrador retrievers, a distraction index of 0.3 is indicative of tight hip joints, and an index of >0.7 is indicative of loose hip joints (passive laxity). Thus, as the distraction index increases from 0.3 to 0.7, the probability of the development of osteoarthritis increases. However, a problem arises in that the outcome for Labradors having a distraction index in this range cannot reliably be predicted (Smith et al., 1993, supra; Lust et al., 1993, *Am. J. Vet. Res.* 54:1990–9). Likely reasons include the other components of the hip joint structure, such as acetabular and femoral head conformation, contribute to functional joint stability and prevent the conversion of intermediate degrees of passive laxity into hip subluxation during ambulation.

Thus, there remains a need for methods which can be used for early diagnosis of dogs affected with canine hip dysplasia, and a need for methods by which functional laxity can be measured in detecting the presence or absence of canine hip dysplasia.

SUMMARY OF THE INVENTION

It is an object of the present invention to provide a method for early diagnosis of dogs affected with canine hip dysplasia.

It is another object of the present invention to provide a method by which functional laxity can be measured in detecting the presence or absence of canine hip dysplasia.

It is a further object of the present invention to provide an apparatus to be employed in the method of the present invention, wherein the apparatus is used for proper positioning of the coxofemoral joints of a dog being evaluated for canine hip dysplasia.

These and further features and advantages of the invention will be better understood from the description of the preferred embodiments when considered in relation to the figures, in which the individual reference numerals denote the same or similar parts or objects throughout the several views:

DETAILED DESCRIPTION OF THE PREFERRED EMBODIMENTS

Definitions

The term "passive laxity" is used herein, for purposes of the specification and claims, to mean the maximal lateral displacement of the femoral heads that occurs when a force is used to distract the hip joint.

The term "functional laxity" is used herein, for purposes of the specification and claims, to mean subluxation of the femoral heads in a hip joint as assessed in a standing position or during ambulation, as modeled by a dog placed in a weight-bearing position.

The term "Ortolani sign" is used herein, for purposes of the specification and claims, to mean the click (sound) that occurs following the abduction of a dog's limb and the reduction of the subluxation (Chalman et al., 1985, *J. Am. Anim. Health Assoc.* 21:671–76). A positive Ortolani sign is thought to be a risk factor for the development of hip joint disease, but the significance of its presence or absence has not been evaluated in long-term studies.

The term "Barlow maneuver" is used herein, for purposes of the specification and claims, to mean the initial maneuvering required to elicit the Ortolani sign, which induces subluxation (Barlow et al., 1962, *J. Bone Joint Surg.* [Br] 44:292–301).

The term "imaging technique" is used herein, for purposes of the specification and claims, to mean dorsoventral radiograph, or computed tomography (CT) images of an individual in hind limb-extended position (e.g., hip-extended CT scans), or a combination thereof.

A method is provided by which functional laxity can be measured for determining the presence or absence of canine hip dysplasia. The method of the present invention is an imaging technique by which hip joint subluxation is assessed of a dog in a weight-bearing position. The degree of dorsolateral subluxation was estimated for each hip joint in this weight-bearing position by measuring the distance between a portion of the femoral head medial to the acetabulum (e.g., lateral-most point of the cranial acetabular rim or, alternatively, to the center of the acetabulum, or from the lateral most point of the dorsal acetabular rim). This measure is reported as the "dorsolateral subluxation score". The dorsolateral subluxation score may be used as a measure of functional laxity and as a predictive indicator where below a selected reference interval of dorsolateral subluxation scores may indicate that a dog has canine hip dysplasia and will likely develop osteoarthritis. The method provides a sensitive measure of hip conformation, and results in the detection of a broad range of subluxation based on the presence or absence of canine hip dysplasia.

For purposes of the description, the methods and compounds of the present invention will be illustrated in the following examples.

EXAMPLE 1

Figure 1:
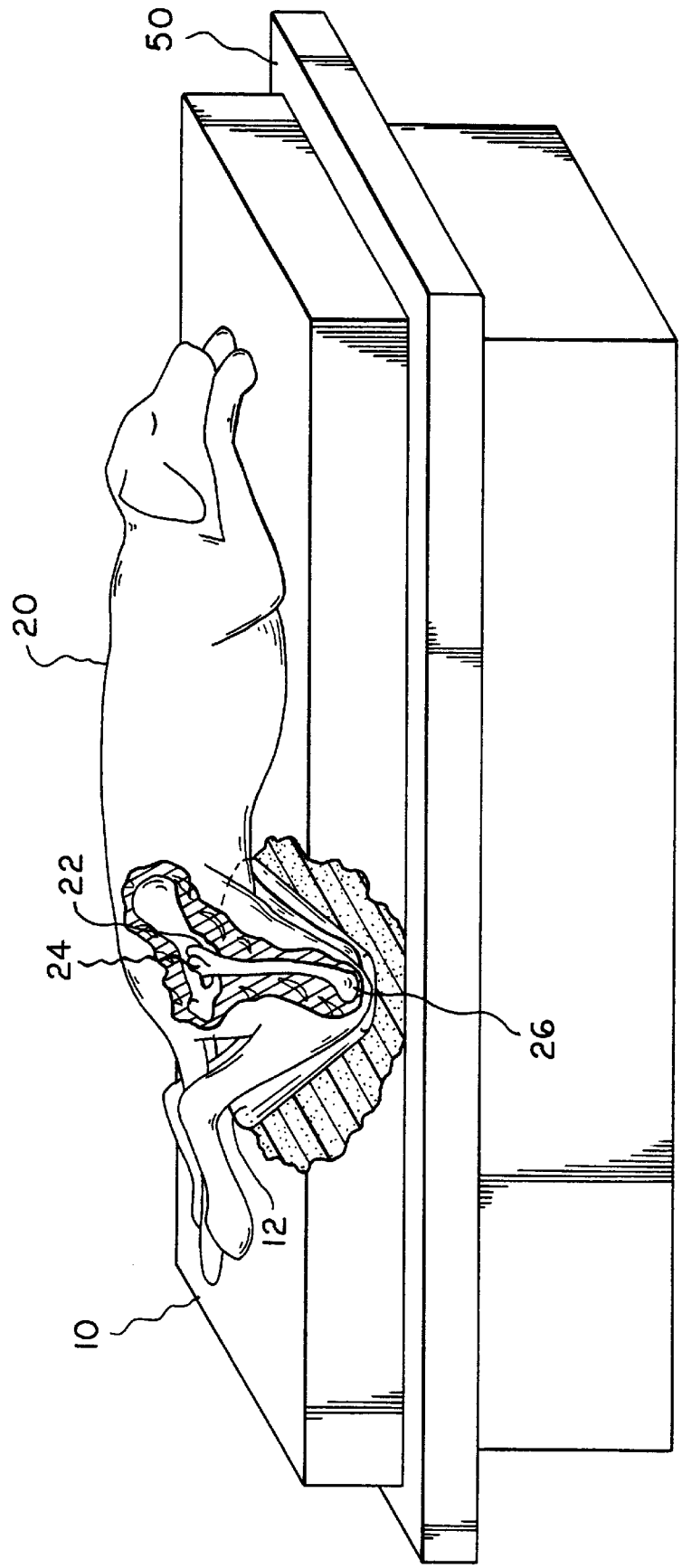
FIG. 1 is a partially schematic view showing the placement of a dog in a weight-bearing position and in relation to the apparatus of the present invention, with a partial sectional view of the hollow body of the apparatus, an with the pelvic bones, femur, and stifles shown for illustrative purposes.

This example illustrates the apparatus employed in the method of the present invention, wherein the apparatus is used for proper positioning of the coxofemoral joints of a dog being evaluated for canine hip dysplasia. Referring now to FIG. 1, apparatus 10 is a base member comprising a pad onto which is placed and positioned dog 20 in sternal recumbency. Apparatus 10 is advantageously used in such a manner so that a substantial portion of the weight of dog 20 is supported by apparatus 10. Apparatus 10 includes a generally cylindrical hollow body 12 extending vertically through apparatus 10, and into which is positioned portions of the hind limbs of dog 20, as illustrated in FIG. 1. In a preferred embodiment, hollow body 12 is a hole which extends vertically and completely through the height of apparatus 10. Apparatus 10 is a generally rectangular piece of impact absorbing material, for example, a foam rubber pad. This padding may comprise a closed cell foam, open cell foam, natural rubbers, synthetic rubbers, or a similar soft, yet supportive material such as a natural or synthetic polymers. As the specific character of the material comprising apparatus 10 does not in and of itself constitute the subject matter of the instant invention, it should be apparent to those skilled in the art that a wide latitude of choice can be exercised in selecting a material suitable for formation and/or fabrication of apparatus 10.

Although one size can easily accommodate a variety of sizes and breeds of dogs, apparatus 10 may be manufactured in various dimensions and assorted sizes in order to accommodate dogs of all heights and sizes. While the height of appartus 10 generally used in the following embodiments was approximately 5 inches, the height of apparatus 10 is not critical and may depend on the body frame and size of dog 20. The precise dimensions are not a limitation of this invention; e.g., the apparatus must simply be able to accommodate a correspondingly sized dog in the manner described herein. Apparatus 10 provides a comfortable cushioned support surface onto which a dog is placed in a generally supine position and with the hind limbs in a generally kneeling position. Apparatus 10 is placed onto a flat, stable surface 50 such as an exam table, or other flat surfaces used in imaging techniques including radiographic and computed tomographic procedures as known to those skilled in the art.

Apparatus 10 is utilized in a manner illustrated in FIG. 1. The hind limbs of anesthetized dog 20 were fixed in an adducted position using securing means, such as medical tape, proximal to the stifles. The hocks were also adducted and held together by securing means. Dog 20 is placed in sternal recumbency in a kneeling position on apparatus 10, with the hock joints extended and stifles flexed and placed into hollow body 12 of apparatus 10. If the size of the hind limbs of dog 20 is such that the they are not in close contact with inner surface of hollow body 12, padding material (e.g., cotton, or other soft material) may be placed between the thighs of dog 20 and inner surface of hollow body 12 to help stabilize the hind-end of dog 20. Hollow body 12 of apparatus 10 provides for a weight-bearing position by allowing each stifle 26 of dog 20 to physically contact flat surface 50 directly, wherein a force is caused to be transmitted along the longitudinal axis of the femur 22 to the hip joints 24 of dog 20, and thereby inducing dorsolateral subluxation. The hips of dog 20 were slightly extended so that the diaphyses were nearly perpendicular to flat surface 50, but not superimposed over the femoral heads or acetabulae. The hocks, hind paws, and trochanters may be checked for symmetry from the lateral and caudal aspects

EXAMPLE 2

This example illustrates the methods according to the present invention in which hip joint subluxation is assessed of a dog in a weight-bearing position. To illustrate this method, several dogs were evaluated. The dogs included fifteen Labrador retrievers (thirteen that ranged in age from 8 months to 12 months; one that was 1.5 years old; and one that was 4.5 years old); three Greyhounds, each 5 years old;

and six Labrador-Greyhound crossbreeds that ranged in age from 11 months to 12 months. The 8 month to 12 month old Labrador retrievers were offspring of matings of parents affected by canine hip dysplasia (e.g., "dysplastic"). A 10 month old, and the 4.5 year old Labrador retrievers were offspring of matings of parents not having canine hip dysplasia ("normal"). The crossbreeds were offspring of dysplastic Labrador retrievers and normal Greyhounds. All of the dogs, under general anesthesia, were tested for the presence or absence of the Ortolani sign.

Before the various imaging techniques were performed, all dogs were premedicated with acepromazine (0.02 mg/kg body weight) and glycopyrrolate (0.01 mg/kg body weight) by intramuscular injection. General anesthesia was induced with thiopental (10 mg/kg body weight, administered intravenously) in the Labradors and crossbreeds, and propofol (6 mg/kg body weight, administered intravenously) in the Greyhounds. Following intubation, inhalant anesthesia (halothane) was used in the Greyhounds to maintain a deep plane of anesthesia so that palpebral and hind limb withdrawal reflexes were absent. Anesthesia in the Labradors and crossbreeds was maintained by intravenous administration of thiopental, and depth of anesthesia was based on the same criteria.

For performing the method according to the present invention, the anesthetized dogs were position using the apparatus and procedures according to Example 1 herein. In the positioning, and as shown in the dorsoventral radiograph representations in FIGS. 2 and 3, the hips of each dog were slightly extended so that the diaphyses 100 were nearly perpendicular to the flat surface supporting the apparatus, but not superimposed over the femoral heads 122 or acetabulae 128. Although the stifles may be obscured by the pad, the user could palpate the greater trochanter and distal lateral femoral epicondyle prior to imaging techniques to check for slight caudal displacement of the stifles relative to the trochanter.

Figure 2:
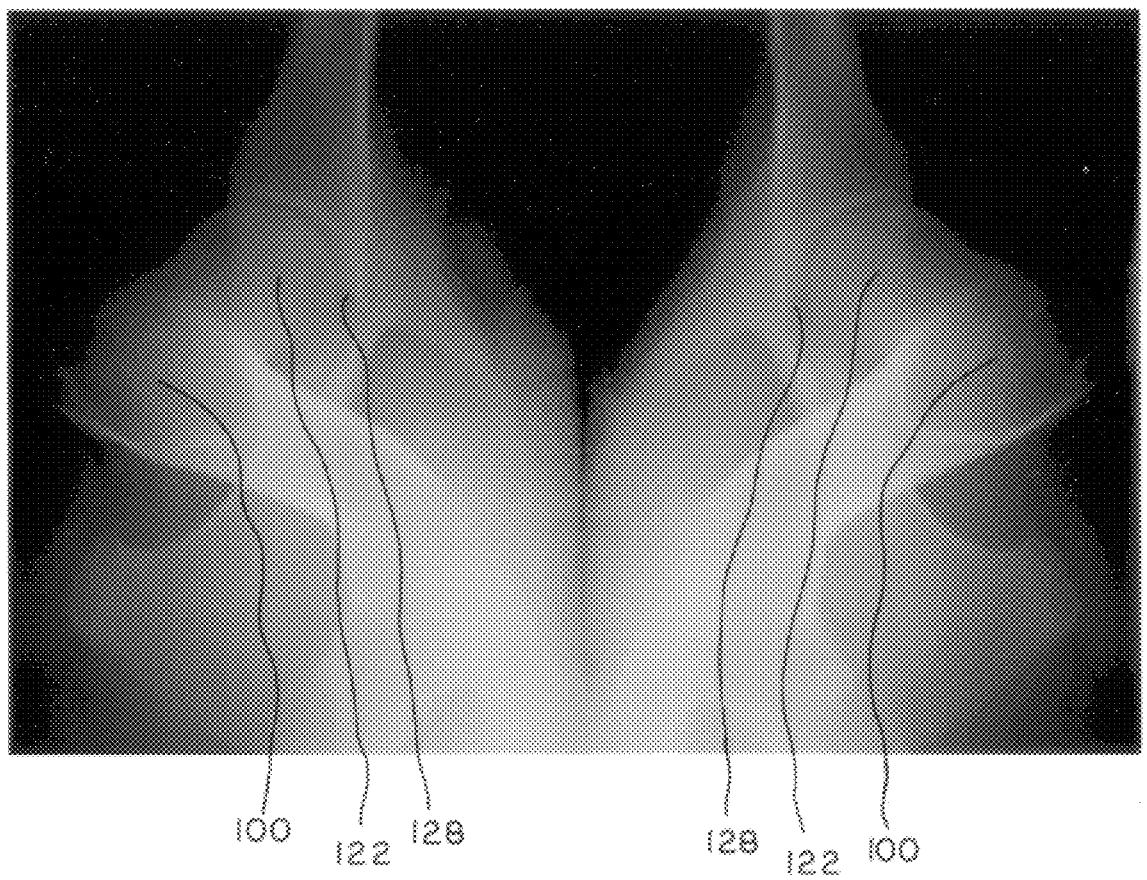
FIG. 2 is a representation of a dorsoventral radiograph of a dog in the weight-bearing position as illustrated in FIG. 1.
Figure 3:
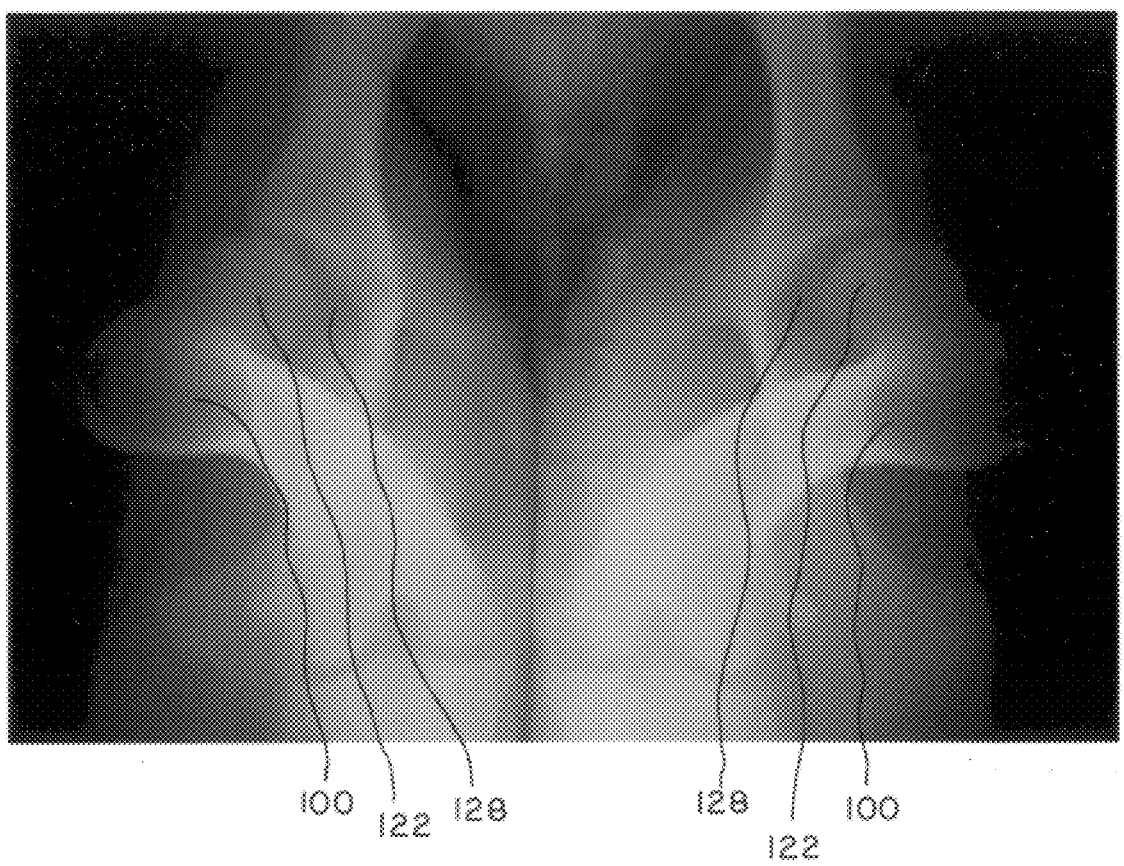
FIG. 3 is a representation of a dorsoventral radiograph of a dog in the weight-bearing position as illustrated in FIG. 1.
Figure 4:
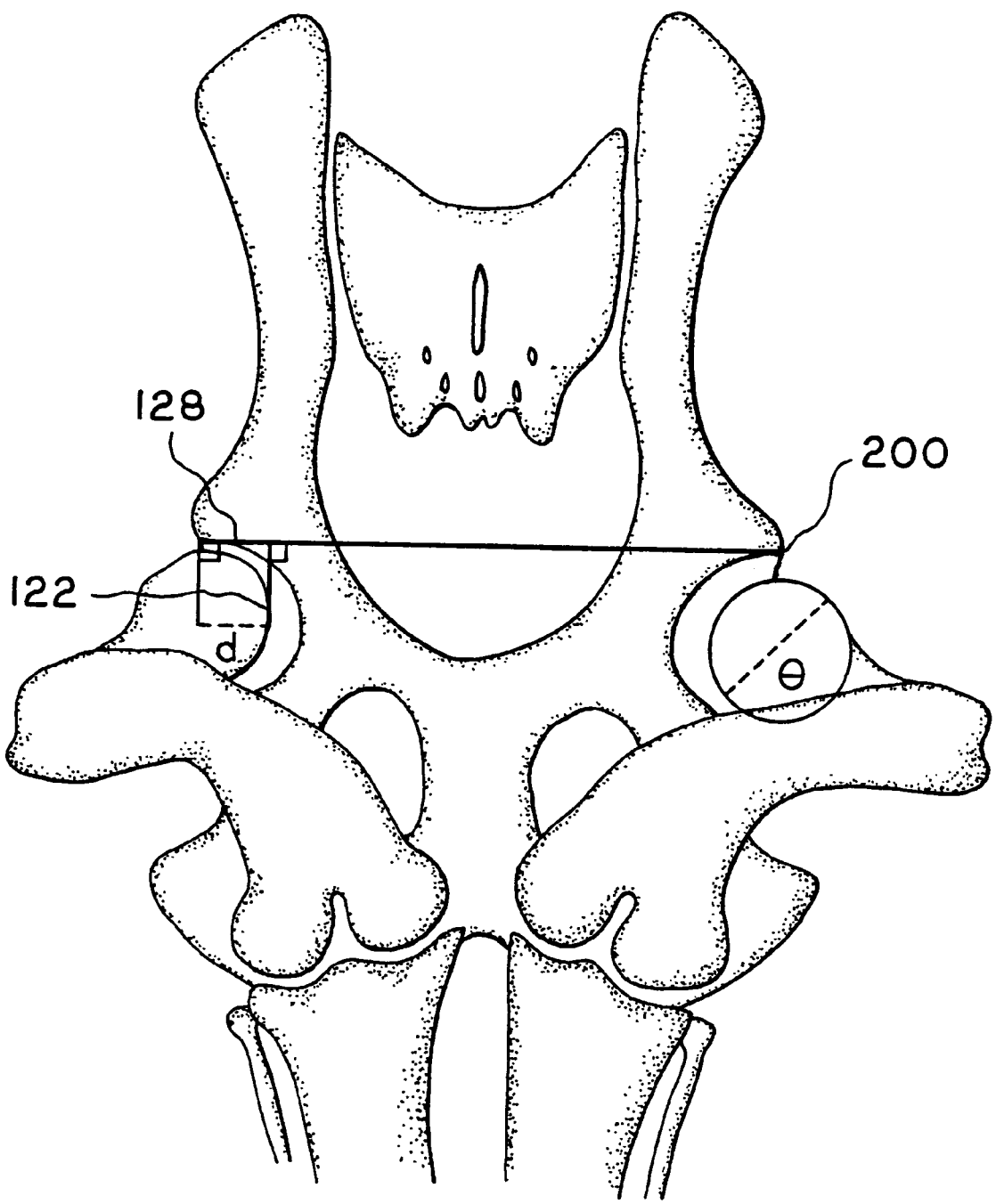
FIG. 4 is a dorsoventral view of a skeletal canine pelvis and femur, illustrating the measurement of the dorsolateral subluxation score by assessing the percentage of the femoral head medial to the cranial acetabulum.

Referring now to FIGS. 2, 3, and 4, in one embodiment of the method of the present invention, the imaging technique comprised dorsoventral radiographs for assessing the degree of dorsolateral subluxation for each hip joint, and revealed dorsolateral subluxation of the femoral head with respect to the acetabulum by stimulating the malarticulation of the hip joint that may occur in a weight bearing position of dogs with canine hip dysplasia. A dorsolateral subluxation score was calculated by measuring the distance between a portion of the femoral head medial to the lateral-most point of the cranial acetabular rim and the lateral-most point of the cranial acetabular rim. Calculation of the dorsolateral subluxation score from a dorsoventral radiograph (using a plastic overlay with the radiograph) is illustrated in the schematic of a radiograph shown in FIG. 4. A straight line 200 joins the cranial acetabular lateral margin. Two perpendicular lines are dropped from straight line 200, one perpendicular line from the most medial edge of femoral head 122, and one perpendicular line from the lateral margin of cranial acetabular 128. The width between the two perpendicular lines is distance, d. The widest diameter of the femoral head is measured and represented by θ. The dorsolateral subluxation score ("DLS score"), or the percentage of femoral head medial to the cranial acetabular view, was determined using the formula:

"$DLS\ score = d \div \theta \times 100$"

Alternatively, the measurement of the DLS score can be made from the center of the acetabulum on the radiograph, rather than the cranial rim of the acetabulum.

Using this method of calculating the DLS score, refer now to FIG. 2. FIG. 2 represents the dorsoventral radiograph of a 5 year old male Greyhound (see Table 1, Dog #4), which has a DLS score of 63% for the left hip, and a DLS score of 67% for the right hip. Using this method of calculating the DLS score, refer now to FIG. 3. FIG. 3 represents the dorsoventral radiograph of a 8 month old dysplastic male Labrador retriever (see Table 1, Dog #18), which has a DLS score of 44% for the left hip, and a DLS score of 41% for the right hip. Thus, as illustrated by FIGS. 2 and 3, the DLS score may be used as a measure of functional laxity and as a predictive indicator where below a selected reference interval of DLS scores may indicate the presence in a dog (e.g., Dog #18) of canine hip dysplasia, and above a selected reference interval of DLS scores may indicate the absence in a dog (e.g., Dog #4) of canine hip dysplasia.

Figure 5:
FIG. 5 is a representation of a central computed tomographic slice of a dog as placed in the weight-bearing position as illustrated in FIG. 1.
Figure 6:
FIG. 6 is a representation of a central computed tomographic slice of a dog as placed in the weight-bearing position as illustrated in FIG. 1.
Figure 7:
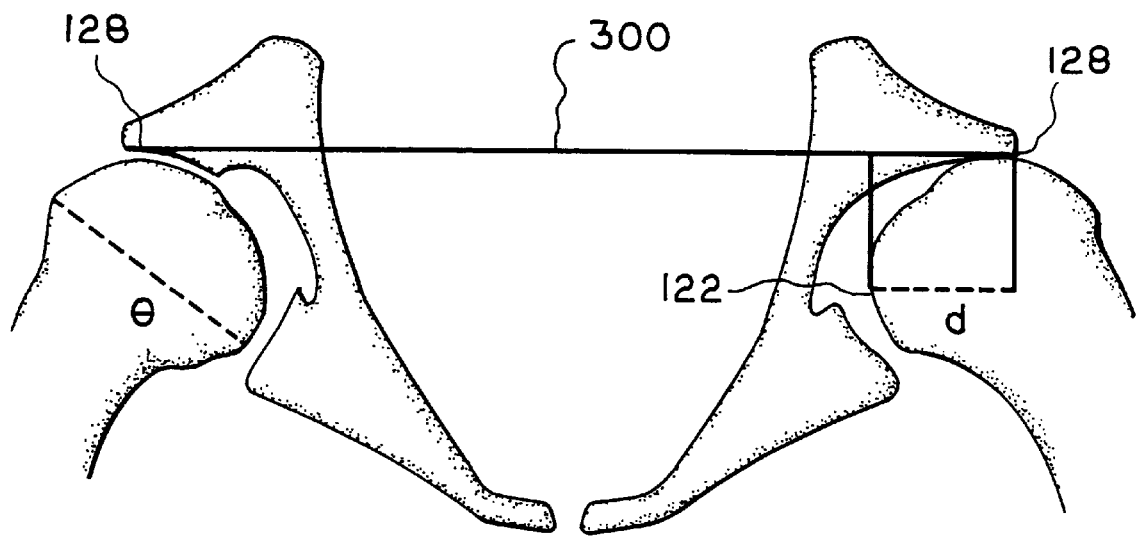
FIG. 7 is a view of a partial skeletal canine pelvis and partial femur, illustrating the measurement of the dorsolateral subluxation score by assessing the percentage of the femoral head medial to the dorsal acetabular rim.

Referring now to FIGS. 5, 6, and 7, in another embodiment of the method of the present invention, the imaging technique comprised CT scans for assessing the degree of dorsolateral subluxation for each hip joint, and revealed dorsolateral subluxation of the femoral head with respect to the acetabulum by stimulating the malarticulation of the hip joint that may occur in a weight bearing position of dogs with canine hip dysplasia. Using the positioning procedures outlined in Example 1, and the anesthetic procedures outlined herein, computed tomography images were obtained of dogs in the weight-bearing position. CT scans were acquired with overlapping, transverse slices of the pelvis at the level of the coxofemoral joints (2 mm thickness, 1 mm index). Images were reconstructed in a 512 by 512 matrix and viewed at bone windows (W=1500, L=250 and W=3200, L=300). Selected images were printed onto radiographic film, and the entire CT study was archived to tape. Additional image viewing, manipulation, three-dimensional image reconstructions and measurements were made on a networked, computer workstation. In referring to FIG. 5, a density phantom 90 may be placed on the dog's pelvis, positioned dorsally on each dog, to obtain data concerning bone density. In the weight-bearing position, the phantom may be loosely secured over the pelvis with securing means, such as Velcro™ straps. For example, a phantom may be 18 inches long, 10 inches wide, 1 ¾ inches in depth, and 7 kg in weight. Gel bags may be placed between the phantom and the dog to improve contact with the phantom and reduce artifacts within the image. In referring to FIG. 6, dogs may also be imaged without using a phantom.

Calculation of the dorsolateral subluxation score from a central CT slice is illustrated in the schematic of a CT scan shown in FIG. 7. A straight line 300 is drawn to connect the lateral-most point of the dorsal acetabular rims 128. Two perpendicular lines are dropped from straight line 300, one perpendicular line from the most medial edge of femoral head 122, and one perpendicular line from the lateral aspect of the dorsal acetabular rim 128. The width between the two perpendicular lines is distance, d. The widest diameter of the femoral head is measured and represented by θ. The dorsolateral subluxation score ("DLS score"), or the percentage of femoral head medial to the dorsal acetabular rim view, was determined using the formula:

"$DLS\ score = d \div \theta \times 100$"

Using this method of calculating the DLS score, refer now to FIG. 5. FIG. 5 represents the CT scan of a 10 month old female Labrador retriever (see Table 1, Dog #9), which has a DLS score of 54% for the left hip, and a DLS score of 57% for the right hip. Note that in this non-dysplastic dog, there is good contact between the lunate surface of acetabulum 128 and the femoral head 122. Using this method of calculating the DLS score, refer now to FIG. 6. FIG. 6 represents the CT scan of a 8 month old dysplastic female Labrador retriever (see Table 1, Dog #23), which has a DLS score of 260 for the left hip, and a DLS score of 24% for the right hip. Note in this dysplastic dog that there is visible severe subluxation of the femoral heads 122. Also note that the lunate surface of the acetabulum 128 has lost its concavity, as compared to that of the non-dysplastic dog shown in FIG. 5. Thus, as illustrated by FIGS. 5 and 6, the DLS score may be used as a measure of functional laxity and as a predictive indicator where below a selected reference interval of dorsolateral subluxation scores may indicate the presence in a dog (e.g., Dog #23) of canine hip dysplasia, and above a selected reference interval of DLS scores may indicate the absence in a dog of canine hip dysplasia (e.g., Dog #9).

EXAMPLE 3

This example illustrates a comparison of the methods according to the present invention in which hip joint subluxation is assessed of a dog in a weight-bearing position, with the compression-distraction stress radiographic method for assessing passive subluxation as described previously (U.S. Pat. No. 5,482,055; Smith et al., 1993, supra). As shown in Table 1, each dog is identified by age at the time radiographs were taken, by sex ("M" for male, and "F" for female), by breed ("G" for Greyhound, "LR" for Labrador retriever, and "Cb" for crossbreed of Labrador×Greyhound cross) The dogs are listed by number representing decreasing order of DLS scores. The distraction method expresses passive subluxation in distraction indices ("DI"). DLS scores are expressed in percentage for radiographs ("R") and CT scans ("CT"). Measurements of the hip include the left hip ("L"), and the right hip ("R"). A subjective hip-extended evaluation was performed as per parameters of the Orthopedic Foundation for Animals (Corley et al., 1989, *Hip dysplasia: a guide for dog breeders and owners*, 2nd edition, Orthopedic Foundation for Animals), expressed as "OFA-like score". The OFA-like score ranges from 1 to 7, wherein 1–3 represents normal; 4 is borderline normal to dysplastic; and 5–7 is dysplastic with 5 being mild and 7 being severe. Also indicated is the presence (+) or absence (−) of osteoarthritis (OA). Indicated is the presence (+) or absence (−) of the Ortolani Sign ("OS").

TABLE 1

| Dog # | Dog | Hip | DLS R | DLS CT | DI | OFA | OA | OS |
|---|---|---|---|---|---|---|---|---|
| 1 | 5 yr. F G | L | 71 | 59 | .15 | 2 | − | − |
| | | R | 71 | 51 | .15 | | − | − |
| 2 | 1 yr. M Cb | L | 68 | 51 | .38 | 1 | − | − |
| | | R | 64 | 49 | .42 | | − | − |
| 3 | 11 mo. M Cb | L | 64 | 52 | .26 | 1 | − | − |
| | | R | 66 | 53 | .30 | | − | − |
| 4 | 5 yr. M G | L | 63 | 57 | .21 | 2 | − | − |
| | | R | 67 | 58 | .21 | | − | − |
| 5 | 5 yr. M G | L | 63 | 53 | .26 | 2 | − | − |
| | | R | 62 | 53 | .30 | | − | − |
| 6 | 11 mo. M Cb | L | 61 | 45 | .33 | 1 | − | − |
| | | R | 67 | 56 | .33 | | − | − |
| 7 | 4.5 yr M LR | L | 68 | 51 | .40 | 3 | − | − |
| | | R | 59 | 44 | .44 | | − | − |
| 8 | 1 yr. F Cb | L | 58 | 41 | .49 | 2 | − | − |
| | | R | 56 | 45 | .49 | | − | − |
| 9 | 10 mo. F LR | L | 58 | 54 | .28 | 2 | − | − |
| | | R | 56 | 57 | .28 | | − | − |
| 10 | 10 mo. M LR | L | 57 | 42 | .58 | 2 | − | − |
| | | R | 56 | 40 | .54 | | − | − |

TABLE 1-continued

| Dog # | Dog | Hip | DLS R | DLS CT | DI | OFA | OA | OS |
|---|---|---|---|---|---|---|---|---|
| 11 | 1 yr. M Cb | L | 59 | 35 | .52 | 2 | − | − |
| | | R | 55 | 37 | .48 | | − | − |
| 12 | 11 mo. F Cb | L | 59 | 53 | .48 | 1 | − | − |
| | | R | 55 | 54 | .32 | | − | − |
| 13 | 1 yr. M LR | L | 50 | 34 | .52 | 6 | + | − |
| | | R | 50 | 33 | .63 | | + | − |
| 14 | 11 mo. F LR | L | 48 | 43 | .61 | 3 | − | + |
| | | R | 54 | 44 | .57 | | − | + |
| 15 | 8 mo. M LR | L | 52 | 33 | .71 | 2 | − | + |
| | | R | 48 | 38 | .67 | | − | + |
| 16 | 1.5 yr. M LR | L | 48 | 37 | .67 | 5 | − | + |
| | | R | 50 | 39 | .67 | | − | + |
| 17 | 8 mo. F LR | L | 54 | 40 | .65 | 2 | − | + |
| | | R | 46 | 37 | .65 | | − | + |
| 18 | 8 mo. M LR | L | 44 | 29 | .68 | 3 | − | + |
| | | R | 41 | 33 | .62 | | − | + |
| 19 | 1 yr. M LR | L | 43 | 31 | .81 | 6 | + | + |
| | | R | 41 | 26 | .88 | | + | + |
| 20 | 11 mo. M LR | L | 40 | 26 | .60 | 5 | − | + |
| | | R | 46 | 29 | .56 | | − | + |
| 21 | 8 mo. M LR | L | 40 | 26 | .80 | 5 | − | + |
| | | R | 37 | 24 | .76 | | − | + |
| 22 | 10 mo. M LR | L | 34 | 29 | .68 | 3 | − | + |
| | | R | 42 | 23 | .60 | | − | + |
| 23 | 8 mo. F LR | L | 30 | 26 | .83 | 5 | − | + |
| | | R | 36 | 29 | .78 | | − | + |
| 24 | 8 mo. F LR | L | 29 | 15 | .91 | 7 | + | + |

As shown in Table 2, the DLS scores were compared to the DI by grouping the joints into four categories according to their probability of developing osteoarthritis (OA), as predicted by the DI in young Labrador retrievers (Lust et al., 1993, supra). Group 1 of 5 dogs are OA-unsusceptible with a DI≦0.3; Group 2 of 6 dogs are OA-susceptible with a 50% chance of developing OA and with a DI between 0.3 to 0.5; Group 3 of 10 dogs are OA-susceptible with greater than a 50% chance of developing OA and with a DI between 0.5 to 0.7; and Group 4 of 5 dogs having a high probability of developing OA, with a DI>0.7. DLS scores are expressed in mean percentage (±standard deviation) for radiographs ("R") and CT scans ("CT") for the group. DI is expressed in mean percentage (±standard deviation) for the group. The OFA-like score is presented as the mean score (±standard deviation) for the group Also indicated is the number of dogs in the group having osteoarthritis (OA). Indicated is the number of dogs in the group having a positive (+) Ortolani Sign ("OS") on at least one hip.

TABLE 2

| Group | DLS R | DLS CT | DI | OFA | OA + | OS + |
|---|---|---|---|---|---|---|
| 1 | 64 ± 1.5 | 55 ± .84 | .24 ± .50 | 2.2 ± .50 | none | none |
| 2 | 61 ± 1.5 | 48 ± 1.8 | .41 ± .02 | 1.7 ± .33 | none | none |
| 3 | 48 ± 1.5 | 35 ± 1.4 | .60 ± .01 | 3.3 ± .47 | 1 | 7 |
| 4 | 39 ± 2.6 | 26 ± 1.9 | .81 ± .02 | 5.0 ± .84 | 2 | 5 |

As illustrated in Table 1, the method of the present invention provides a practical and reproducible method for assessing hip joint subluxation in a dog in a weight-bearing position. The DLS scores measured by the radiographic procedures embodying the present invention ranged from 29% to 71%. As illustrated in Table 2, hip joints considered OA-unsusceptible (Group 1), and hence the absence of canine hip dysplasia, had a mean LS score of 64% (range 56% to 71%); hip joints considered OA-susceptible with a less than 50% chance of developing osteoarthritis (Group 2) had a mean DLS score of 61%; hip joints considered OA-susceptible, and hence presence of canine hip dysplasia, with a greater than 50% chance of developing osteoarthritis (Group 3) had a mean DLS score of 48%; and hip joints considered a high probability for developing osteoarthritis (Group 4), and hence the presence of canine hip dysplasia, had a mean DLS score of 39%. Thus, Table 2 clearly shows a correlation between the DLS scores, as determined by the method according to the present invention, and the susceptibility to canine hip dysplasia. Therefore, the DLS scores may be used as a measure of functional laxity and as a predictive indicator where below a selected reference interval of DLS scores may indicate the presence in a dog of canine hip dysplasia (and probability of subsequently developing osteoarthritis), and above a selected reference interval of DLS scores may indicate the absence in a dog of canine hip dysplasia (and probability of not subsequently developing osteoarthritis).

As illustrated in Tables 1 and 2, all of the hips considered OA-unsusceptible (DLS score≧56%; see, e.g., Group 1) were also considered normal by the subjective OFA-like evaluation of the hip-extended projection. However, five of the Labrador retrievers considered normal by OFA-like evaluation had at least one joint with a DLS score of≦48% (see, e.g., Table 1, dog #s 14, 15, 17, 18, and 22). Such a DLS score places them in a group considered to be OA-susceptible with a 50% chance of developing osteoarthritis. Since all 5 of these dogs are less than one year old, this result is an indication that the method of assessing dorsolateral subluxation can be used for earlier diagnosis of canine hip dysplasia than the hip-extended view. Further, the method of the present invention can detect changes associated with the earliest lesions (perifoveal cartilage, fibrillation, synovitis, and synovial effusion) associated with osteoarthritis in the hips of dysplastic dogs which are not appreciated on a standard radiograph of the hip joint.

Figure 8:
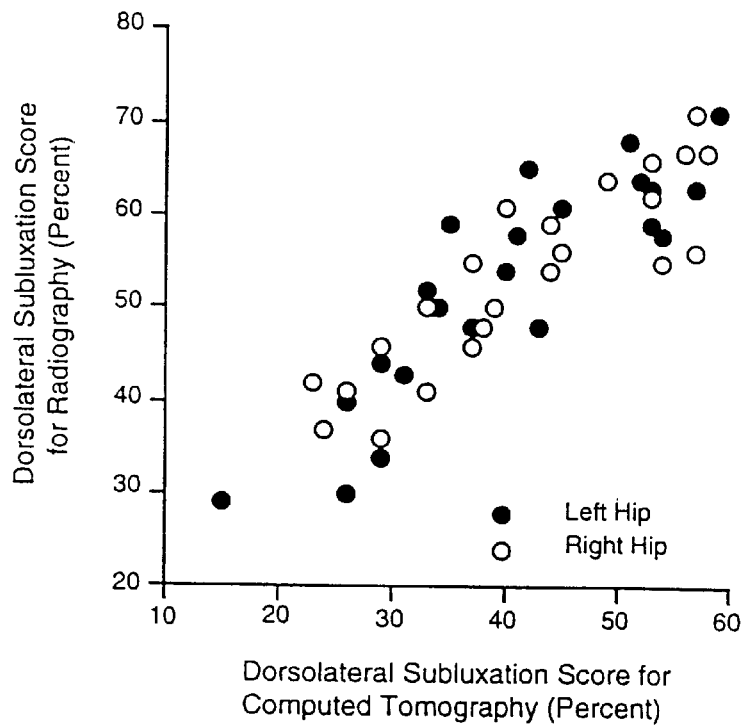
FIG. 8 is a graph showing the relationship between the dorsolateral subluxation score measured using radiography to that measured by computed tomography for each hip joint.

Comparing the mean DLS scores as measured by the radiograph technique and as measured by the CT scan technique reveals that the mean DLS scores as measured by the CT scan technique for the four groups are approximately 12% lower. The difference is likely a result of measuring the DLS score at the center of the acetabulum on the CT scans, as opposed to the more laterally located cranial acetabular rim on the radiograph. However, the high correlation between the measurements of DLS scores as determined by radiograph and as determined by CT scans indicates that the scores from the two different imaging techniques in the weight-bearing position is reproducible. The correlation analysis was performed by determining the Pearson product-moment correlation coefficient ("r") separately for each hip joint, and also by intraclass correlation analysis. As shown in FIG. 8, the correlation coefficient (r)=0.89 for both the left and right hips.

Figure 9:
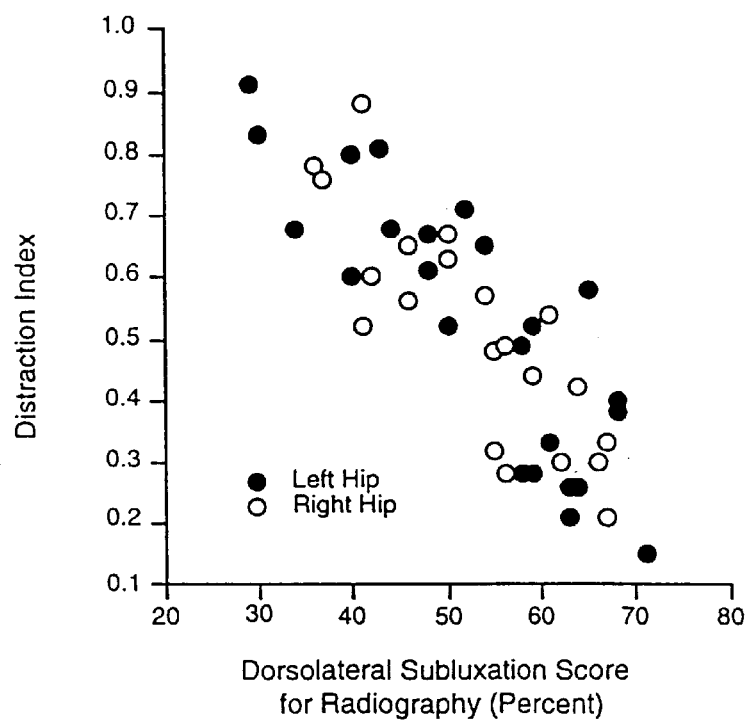
FIG. 9 is a graph showing the relationship between the dorsolateral subluxation score measured using radiography and the distraction indices for each hip joint.

The relationship between the DLS score to the DI groupings was also subjected to correlation analysis. As shown in FIG. 9, the DLS score showed statistical correlation with the DI ($r=-0.87$ for both hips; $p<0.05$) which means that 76% of the variation in the DLS score can be explained by a variation in DI. As shown in Table 1, the DI ranged from 0.15 to 0.91. Each hip joint with a DI≦0.3 had a DLS score≧56%. Three hips that had a DLS score of≧56% had a DI which placed them in the OA-susceptible group with a greater than 50% chance of developing osteoarthritis (DI in a range between 0.5 to 0.7); and nine hips that had a DLS score of≧56% also had a DI which placed them into the OA-susceptible group with less than 50% chance of developing osteoarthritis (DI in a range of 0.3 to 0.5). These differences in groupings of susceptibility to the development of osteoarthritis, evident from the comparison of the method of the present invention to the distraction method, may reflect different parameters measured by each method which are important in the pathogenesis of canine hip dysplasia and subsequent development of osteoarthritis.

A positive Ortolani sign is thought to be a risk factor for the development of hip joint disease. As shown in Tables 1 and 2, where the DLS score is greater than 50%, a positive Ortolani sign for a given hip was rare; e.g., only 2 of 28 hips. Every hip joint with a DLS score of less than 50% had a positive Ortolani sign. This is an additional indication that dogs having a DLS score of less than 50%, as detected by the method of the present invention, have at least a moderate susceptibility of having or developing canine hip dysplasia.

In summary, the method according to the present invention provides for the measurement of functional laxity in detecting the presence or absence of canine hip dysplasia, and the probability developing osteoarthritis associated therewith. The method of the present invention technique by which hip joint subluxation is assessed of a dog in a weight-bearing position comprises an imaging technique selected from the group consisting of a radiographic technique, a computed tomographic technique, or a combination thereof. The degree of dorsolateral subluxation was estimated for each hip joint in this weight-bearing position by measuring the distance between a portion of the femoral head medial to the acetabulum (e.g., as measured from the center of the acetabulum, or from the lateral most point of the cranial acetabular rim, or from the lateral most point of the dorsal acetabular rim) and the acetabulum. This measure is reported as the "dorsolateral subluxation score". The DLS scores may be used as a measure of functional laxity and as a predictive indicator where below a selected reference interval of DLS scores may indicate the presence in a dog of canine hip dysplasia (and probability of subsequently developing osteoarthritis), and above a selected reference interval of DLS scores may indicate the absence in a dog of canine hip dysplasia (and probability of not subsequently developing osteoarthritis). As appreciated by those skilled in the art, such reference intervals may vary between breeds of dogs because of such factors including, but not limited to, size and bone structure.

While the radiograph technique may be more practical for veterinarians to perform, and therefore a preferable method for assessing canine hip dysplasia according to the present invention, the computed tomographic technique additionally allows for determination of bone density and the evaluation of the contribution of hip geometry to coxofemoral reduction. With respect to Labrador retrievers, a DLS score (as determined by the radiographic technique) of greater than 60% suggests that canine hip dysplasia is absent in the dog, and the dog is unsusceptible or has a low susceptibility for developing osteoarthritis; a DLS score of less than 50% suggests a moderate susceptibility for developing osteoarthritis; and a DLS score of less than 40% suggests the presence of canine hip dysplasia in a dog and a high probability of that dog for developing osteoarthritis.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method for measuring functional laxity in a dog for determining presence of or absence of canine hip dysplasia comprising the steps of:
   (a) placing the dog in a weight-bearing position causing the positioned dog to assume a kneeling position;
   (b) obtaining an image of the hip joint by an imaging technique selected from the group consisting of a radiographic technique, a computed tomographic technique, and a combination thereof;
   (c) determining from the image of the hip joint a dorsolateral subluxation score (DLS score) for each hip joint of the positioned dog; and
   (d) comparing the dorsolateral subluxation score from (c) with selected reference intervals of dorsolateral subluxation score to predict either the presence of or absence of canine hip dysplasia.

2. The method of claim 1, wherein the dog is positioned in a weight bearing position by using an apparatus comprising:
   a base member that supports a dog in sternal recumbency; and
   a generally cylindrical hollow body extending vertically through the apparatus, wherein positionable into the hollow body are portions or hind limbs of the dog thereby causing a positioned dog to assume a kneeling position.

3. The method of claim 1, wherein the imaging technique is a radiographic technique comprising dorsoventral radiography.

4. The method of claim 1, wherein the imaging technique is a computed tomographic technique comprising computed tomographic scans of a pelvis of the dog, and at a level of coxofemoral joints.

5. The method of claim 1, wherein the image is obtained by a radiographic technique and the DLS score is determined by measuring the distance between a portion of femoral head medial to the cranial acetabulum rim and the cranial acetabulum rim.

6. The method of claim 1, wherein the image is obtained by a radiographic technique and the DLS score is determined by measuring the distance between a portion of femoral head medial to the center point of the acetabulum and the center point of the acetabulum.

7. The method of claim 1, wherein the image is obtained by a computed tomographic technique and the DLS score is determined by measuring the distance between a portion of femoral head medial to the lateral-most point of the dorsal acetabular rim and the lateral-most point of the dorsal acetabular rim.

8. The method of claim 7, wherein the computed tomographic technique comprises computed tomographic scans of a pelvis of the dog, and at a level of coxofemoral joints.

9. The method of claim 1, wherein the image is obtained by a computed tomographic technique and the DLS score is determined by measuring the distance between a portion of femoral head medial to the center point of the acetabulum and the center point of the acetabulum.

10. The method of claim 9, wherein the computed tomographic technique comprises computed tomographic scans of a pelvis of the dog, and at a level of coxofemoral joints.

* * * * *